United States Patent [19]

Reggio

[11] Patent Number: 4,613,515

[45] Date of Patent: Sep. 23, 1986

[54] FINGERPRINT DEVELOPMENT KIT AND PROCESS

[75] Inventor: Carl J. Reggio, New York, N.Y.

[73] Assignee: Apple Adhesives, Inc., Hollis, N.Y.

[21] Appl. No.: 599,886

[22] Filed: Apr. 13, 1984

Related U.S. Application Data

[63] Continuation-in-part of Ser. No. 584,653, Feb. 29, 1984, abandoned.

[51] Int. Cl.$^4$ ............................ A61B 5/10; B41K 1/00
[52] U.S. Cl. ........................................ 427/1; 118/315; 118/719; 118/733; 427/145; 427/255.4
[58] Field of Search .................... 427/1, 145, 255.4; 118/31.5, 719, 733

[56] References Cited

U.S. PATENT DOCUMENTS

| | | | |
|---|---|---|---|
| 4,297,383 | 10/1981 | Bourdon | 427/1 |
| 4,407,842 | 10/1983 | Shepard | 427/1 |
| 4,461,235 | 7/1984 | Morton | 427/1 |

FOREIGN PATENT DOCUMENTS 767341  1/1957  United Kingdom .................... 427/1

Primary Examiner—Norman Morgenstern
Assistant Examiner—Janyce A. Bell
Attorney, Agent, or Firm—Paul J. Sutton

[57] ABSTRACT

This invention relates to a new means, generally in kit form, for developing into a visible form fingerprints left on a solid surface, based upon the generation of a vapor-like phase of a cyanoacrylate material, alone or with functionally enhancing additives. This invention further relates to a process utilizing the exothermic polymerization reaction of cyanoacrylate compound, to generate a conjugable vapor-like phase.

14 Claims, No Drawings

FINGERPRINT DEVELOPMENT KIT AND PROCESS

This is a continuation-in-part of U.S. application Ser. No. 584,653, filed Feb. 29, 1984 now abandoned.

DESCRIPTION OF THE PRIOR ART

The preparation of cyanoacrylate polymers, especially as adhesives, is well known, and they have been used as such for many years. Such cyanoacrylate polymers include the polymers of alkyl esters, carboxyalkyl esters, alkoxyalkyl esters and other hydrocarbyl esters of 2-cyanoacrylic acid. In addition, other derivatives of cyanoacrylic acid, such as the cyanoacetamides have been used as monomer, or as polymer precursors. These various compounds are disclosed, for example, in the following U.S. patents: U.S. Pat. Nos. 3,759,264, 3,5559,652, 3,564,078, 3,995,641 and 3,711,448.

Generally, the desirability of these various compounds for use as adhesives rests upon the fact of their rapid polymerization under suitable conditions and, equally important, the fact that the precise speed of the reaction can be controlled by a combination of secondary additives, such as initiators, promoters and accelerators on the one hand, or inhibitors on the other hand. It has also been discussed that these compounds are known to polymerize exothermically, but in the past, this exothermic reaction, especially for the compounds used in the surgical adhesive field, has been considered a problem.

It has recently been learned that when the polymerization is permitted to occur in an open environment, the exothermic reaction does generate a vapor-like phase, known as "microcrystalline vapor", which comprises at least partially polymerized cyanoacrylate compounds.

SUMMARY OF THE INVENTION

In accordance with the present invention, kit means are provided for rendering visible, and providing for the permanent recording of, even faint or latent fingerprints from almost any solid surface, utilizing the exothermic polymerization reaction of a α-cyanoacrylate compound in an open location adjacent the suspected fingerprint location. This invention further provides a process for generating and developing such visible fingerprints.

The kit comprises an absorbent, generally inert pad having sorbed therewith a cyanoacrylic polymerization catalyst, including one or more of an initiator, a promoter and an accelerator; plus optionally, an inhibitor compound. In addition, there is also sorbed with the inert pad at least one of the following print enhancing agents capable of conjugating with the amino acids or fatty acids of the fingerprints, including: a fluorescent labeling compound; a silization agent which can preferably penetrate through any fatty acid overlayer; and an active conjugating agent capable of conjugating with the amino group of an amino acid, such as an active hydrazide compound other suitable material. The kit also provides a separate source of a polymerizable alpha-cyanoacrylate monomer, or mixtures of such monomers, optionally including at least one inhibitor agent. In accordance with the process of this invention, a cyanoacrylate monomer, or prepolymer, is added to the surface of the sorbent pad and the pad is placed adjacent a location believed to contain desired fingerprints. The pad is permitted to remain undisturbed while the cyanoacrylate compound polymerizes on the pad and during such exothermic polymerization generates a microcrystalline vapor phase. The microcrystalline vapor is then permitted to travel, as by convection, through the atmosphere to a solid surface; the vapor can make contact with the latent fingerprint condition on the solid surface.

When reference is made to a "latent fingerprint condition" it is intended to encompass the usual residue of α-amino acids, urea, salt, and riboflavine; as well as fatty acids, remaining after contact between a solid surface and a human finger or hand. In addition, the unusually sensitive fingerprint developing system in accordance with this invention can also develop a fingerprint created by the residual condensed moisture remaining after contact between a human hand, or finger, clad in a thin, skin-tight plastic (e.g. polyethylene) glove.

Most comprehensively, this invention comprises an inert cellulosic, absorbent pad, generally having a weight of at least about 1 gram and preferably not greater than about 4 grams, dry, and having an external macro surface area of at least about 2 square inches, and generally need not be greater than about 16 square inches. The pad has been cleaned to remove any extraneous material and then has absorbed thereinto a catalytic amount of a catalyst for 2-cyanoacrylate polymerization. The pad is preferably formed of natural cellulosic material, such as cotton, flax, jute, and most preferably, fibrous such materials, optimally woven into a structurally coherent thin, multi-layer form. The catalyst is generally added, most easily, to the pad in a solution, especially when the catalyst is a solid material. Even when a liquid, however, because of the relatively small quantity of the catalyst to be added, in order to assure a relatively uniform distribution of the catalyst throughout the pad, it is preferred that a relatively dilute solution of the catalyst in an inert more volatile solvent, e.g., methanol, be sorbed onto the pad, and the pad then permitted to dry by evaporation of the solvent, leaving the catalyst behind on the pad.

Useful catalysts, including initiators, promoters and accelerators are generally basic compounds such as inorganic bases: sodium carbonate, calcium carbonate, sodium bicarbonate, potassium peroxodisulphate, magnesium oxide, or sodium hydroxide. Organic compounds: including the metallic salts of carboxylic acids, such as copper naphthenate, copper acetylacetonate, sodium stearate, or sodium acetate. Organic amines and their salts, can also be used such as: aniline, dibutyl amine, diamino propane, triethyl amine, piperidine, 2-(N-ethylanilino)ethanol, triethylene tetramine, tetraethylene pentamine, diethanolamine, triethanolamine, benzylamine, N,N-dimethyl-p-toluidine, N,N-dimethylaniline, imidazole, triethylenediamino, methyl-dicyclohexylamine, N,N-dimethyl-cyclohexylamine, tetramethyl iminobispropylamine, DBU-phenol salt, DBU-2 ethyl hexane acid salt, N-butylaldehyde aniline, N-dialkyl and N-alkyl anilines, such as N-ethyl aniline, N-diethyl aniline, polyoxethylene alkylamine, or ammonium salts such as: alkyl isoquinoliniumbromamide, 2-hydroxy-3-methacryl hydroxypropyl trimethyl ammonium chloride, tetradecyldimethyl ammonium chloride, dodecyl trimethyl ammonium chloride, distearyl dimethyl ammonium chloride, tetrabutyl ammonium bromamide, N-benzyl picolinium chloride, N-lauryl-4-picolinium chloride, N-lauryl pyridinium chloride, or oleic acetate salt or fatty acid N-alkylol amines, and the HCl salt of each such amine.

A cyanoacrylate monomer or polymer precursor, such as is derived from, a cyanoacrylate having the following general formula, for example, can be used:

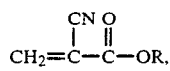

wherein R can be, for example, a hydrocarbyl group such as alkyl, aryl, aralkyl, alkaryl, cycloalkyl, and substituted such groups, e.g., allyl, ethyl, methyl, n-butyl and isobutyl. Useful such materials include a mixture of longer and shorter chain polymers having viscosities of from about 2–3 cps up to about 60–80 cps. The further reaction rate of polymerization will be slowed with increasing chain lengths.

The cyanoacrylate monomer or polymer precursor is added to the pad in an amount sufficient to react totally in a time perid no shorter than about 1½ minutes duration, and to generate, by the end of that time, a pad temperature, without external heating, of at least about 80° and generally not greater than about 140° C., in an ambient temperature of 20° C. This temperature range will generate the microcrystalline vapor which will then be carried to the latent fingerprint site by convection, within a radius of up to from about 3 to about 6 feet from the pad. Preferably from about 1 to about 8 grams of cyanoacrylate monomer is added to each pad, and most preferably from about 1 to about 6 grams per pad.

Because of the relatively reactive nature of most cyanoacrylate monomers or prepolymers, the cyanoacrylate compound can also contain an inhibitor, both to improve its long-term storage, and to provide control for the polymerization reaction after contact is made with the catalyst on the pad. Useful inhibitor materials can generally be described as, preferably, Lewis acids, such as hydroquinone, short chain-hydrocarbyl carboxylic acids, and phenol compounds, such as 2,4,6-tris(-dimethyl aminomethyl)phenol.

It is not believed necessary to provide a complete listing of all polymerizable cyanoacrylate monomers and prepolymers, or the catalysts, accelerators, promoters or initiators, or inhibitors, for such materials, as the polymerization of these compounds is well known to the art. For purposes of this invention, the criterion is the generation of a sufficient rate of microcrystalline vapor to develop the latent fingerprints, and, in the optional modes of this invention, to act as a carrier for the remaining active materials on the pad. It has been found that if the polymerization reaction occurs at a sufficient rate, so as to generate a temperature in the range of preferably from about 80° to about 130° C. within 1½ minutes, and to continue the reaction at that temperature preferably for at least another minute and most preferably for up to an additional 1 to 4 minutes, sufficient microcrystalline cyanoacrylate vapor is generated for purposes of developing the fingerprints in accordance with this invention.

As a further unexpected advance, it has been discovered that certain other compounds which enhance the visibility and reproducibility of the developed fingerprints can also be carried by the microcrystalline vapor to the latent fingerprint location. These enhancement additives must have a vapor pressure (at the temperature developed on the pad by the exothermic polymerization), either alone or in the presence of the microcrystalline vapor, sufficient to enable them to be carried in sufficient quantity from the pad to the latent fingerprint site. These enhancement additives must be stable at the exothermic reaction temperatures for the cyanoacrylic compounds, i.e., in the range of from about 80° to about 140° C., and be non-reactive with the cyanoacrylic compound or polymer, but be sufficiently attracted to the cyanoacrylate as to be carried together with it in the microcrystalline vapor form, even if the vapor pressure of the enhancement additive is insufficient in and of itself.

It is understood that the majority of amino acids that would form the latent human fingerprint are alpha-amino acids, such as tyrosine and thereby have a similar reactive carbon site as is present in the alpha-cyanoacrylic acid compound. Thus, these enhancement additives can conjugate with the alpha-cyanoacrylate in the microcrystalline vapor state, but then should have a preferential attraction toward the amino acid, so as to be transferred to the amino acid when contact is made between the cyanoacrylate microcrystalline vapor and the amino acid. These enhancing or secondary additives are generally of two types: first, the immediate enhancement additives react with or conjugate with amio acid or with fatty acid residues from the fingerprint contact to form opaque white or colored compounds, and fluorescent compounds, which in turn are more readily visible and reproducible. A second group assists the active conjugating agents to make contact with the active site on the amino acid molecules. The second group of compounds are generally extremely potent, preferably polar, solvents for the film of oil, or higher fatty acids, which may overlay or form a protective film over, the active amino acid residue.

The most effective fingerprint development enhancing materials are those generally known as fluorescent labeling compounds. These fluorescing agents are especially useful in rendering visible that would otherwise be an only weakly developed fingerprint. Such fluorescent compounds can preferably be present on the pad and are carried with the cyanoacrylate microcrystalline vapor to the fingerprint site. The fluorescent compound is preferably present on the pad in an amount of at least about 0.01 gram per gram of cyanoacrylate compound added to the pad. Generally not more than about 0.05 gram of fluorescent compound per gram of cyanoacrylate compound is required. Such fluorescing compounds should not be reactive with the cyanoacrylate material, or with the various inhibitor and catalytic agents on the pad; these compounds must be able to be carried by the cyanoacrylate microcrystalline vapor, but have a greater affinity for amino acids or carboxylic fatty acids. Examples of such fluorescence-producing labeling compounds, which are either themselves fluorescent or which interact with the fingerprint target materials (e.g., amino acids) to form a fluorescent material, include, N-(3-pyrene)maleimide, 7-(4-methoxy)-benzyl amino-4-nitro-2-oxa-1,3-diazole; and dimethyl amino-1-naphthalene sulfonylhydrazide; and 2'-azido-2'-deoxy uridine, N(1-anilino-napthyl)-4-maleimide, o-phthaldehyde and fluorescamine, fluorescein, dibromofluorescein, and dimethyl-fluorescein. The latter materials require the presence of a polar organic solvent, such as DMSO, or di-n-butyl formamide. Preferably, diethyl phthalate can also be present as a secondary solvent.

Useful conjugating agents which serve to further enhance the development of a fingerprint by also conjugating with the amino acid groups, include, for example, reactive hydrazide compounds which can be carried by the cyanoacrylate microcrystalline vapor to conjugate with the amino group. The active hydrazides generally have as a formula:

$$R_1-N=N-R_2$$

wherein each of $R_1$ and $R_2$ is a hydrogen atom, an organic group, or a halogen atom; at least one of $R_1$ and $R_2$ preferably is an aryl group.

The hydrazide is preferably a liquid or allow melting point solid at room temperature, and has a sufficient vapor pressure at the exothermic reaction temperatures of the cyanoacrylate compound, in the context of this invention, to be carried over with the microcrystalline vapor to the latent fingerprints. Examples of such hydrazide materials include isonicotinic hydrazide, nicotinic hydrazide, p-toluene sulfonyl hydrazide, phenyl hydrazide, and diphenyl hydrazide.

It has also been found that the organic silyl compounds, which silizate amino acids and, where present, fatty acids, are highly effective conjugating agents. They possess sufficient solvent activity to penetrate an oily fatty acid residue above the amino acid and also have the desired vapor pressure in the temperature range of from about 80° to about 140° C. to be carried over with the microcrystalline vapor. The preferred silization agents are the alkyl silyl compounds, especially the methyl silyl compounds, e.g., having the formula:

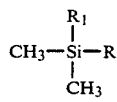

$$CH_3-\underset{\underset{CH_3}{|}}{\overset{\overset{R_1}{|}}{Si}}-R$$

wherein $R_1$ is a hydrogen or a methyl group, or substituted methyl group and R can be, for example, a halogen atom, or an organic group, such as a carbamide group, an azine, or an aromatic group; any of these organic groups may also include additional silyl groups. R is preferably a nitrogen-substituted organic group or a halogen; preferred compounds include trimethyl-silyl chloride, trimethyl silyl acetamide, trimethyl silyl imidazole, trimethyl silyl-methylacetamide, isopropenyloxy trimethylsilane; N-trimethylsilyl diethylamine; N-trimethylsilyl dimethylamine; N,O-bis(trimethylsilyl)carbamate; N-trimethylsilyl-N-methyl heptafluorobutyramide; N-trimethylsilyl-N-methyl trifluoroacetamide; bis(chloromethyl)tetramethyl disilazane; dimethyl monochloriosilane; N,O-bis(dimethyl silyl)acetamide; tetramethyl disilazane; chlormethyl dimethyl chlorosilane; dimethyl dichlorosilane; TMSI-D* Reagent (i.e., dimethyl formamide, hexamethyl disilazane, trimethylchlorosilane, in the weight ratio of 4:4:1); TMSI-P* Reagent (i.e., o-pyridine, hexamethyl disilazane and trimethyl chlorosilane, in the weight ratio of 9:3:1); TMSI-S* Reagent (i.e., bis(trimethylsilyl)trifluoroacetamide, trimethylchlorosilane, and trimethylsilyl amidazole). These silyl compounds react with amino acids to form a bluish opaque finely detailed print. The silyl compounds also assist in penetration through any oily fatty acid barrier on top of the amino acid residue and can carry with them, e.g., the hydrazides. The silyl compounds containing a nitrogen-substituted R-group can act in a dual role as amino-acid reagent and as an accelerator for the cyanoacrylate polymerization reaction.

*Trademark of Serva Biochemical

A variety of organic solvents having a sufficient vapor pressure at operating temperatures, being sufficiently compatible with the cyanoacrylate microcrystalline vapor and which have the effect of solvating the conjugating compounds can also be present, generally sorbed to the pad, prior to the addition of the cyanoacrylate on the pad to improve carry-over with the microcrystalline vapor, and to improve penetration by the conjugating compounds through any oily film over the fingerprints. Examples of such agents include dimethyl sulfoxide (DMSO), diethyl phthalate ("DEP"), and dibutyl formamide.

To further enhance the fluorescing effect of, for example, the fluorescent indicator compounds, a hydrogen chloride organic salt compound which would react at the fingerprint site to release HCl, should also be present. Such materials include, for example, as the catalyst material for the polymerization of the cyanoacrylate compound, an alkanolamine hydrochloride, imidazole hydrochloride, or diethylamine hydrochloride.

The enhancing additives are each generally present on the pad in an amount of at least about 0.1 gm. per gram of cyanoacrylate compound added, preferably at least about 0.2 gm., and most preferably from about 0.2 gm. to about 0.6 gm. per gram of cyanoacrylate monomer or polymer precursor.

The active materials of this invention are sorbed onto the pad, preferably as a solution in, e.g., methanol. The solution can contain at least about 1 gram of the conjugating agent or combinations of such agents, preferably at least about 2 grams, up to about 5 grams per 100 ml. of solvent. The fluorescent materials can be present in any amount of about at least 0.1 gm/100 ml. of solution, generally not more than about 0.5 gm/100 ml., i.e., a weight ratio of about 1:10 for the conjugating agent-to-the fluorescent agent.

The organic solvents, such as DMSO, can be present in the methanol solution in amounts of at least about 1 gm/100 ml., and generally more than about 3 gm./100 ml. is unnecessary.

The accelerators and catalysts can be present in an amount of preferably at least about 0.1 gm./100 ml. methanol and generally is not required in amounts greater than 1.0 gm./100 ml.

Preferably, in a kit form, inert solid pads having sorbed thereon all of the desired ingredients except the cyanoacrylate monomer, or polymer precursor, are individually packaged. When the fingerprint site is reached and a determination of whether a fingerprint is present is to be made, a sealed package is broken open, the pad removed and placed adjacent the solid surface to be tested. The cyanoacrylate monomer, or polymer precursor, is then applied to the pad in a suitable amount and the pad permitted to rest adjacent the latent fingerprint site. Within not more than 8 minutes, any latent fingerprints located within approximately 3 to 5 feet of the fingerprint pad will be developed. It is preferred that in the kit, the cyanoacrylate monomer is packaged in a sealed container, most preferably a single aliquot being individually packaged in a sealed container such that only a single dose is exposed to the air when a single pad is to be used. The cyanoacrylate, monomer, or polymer precursor, preferably also contains a suitable inhibitor agent as defined above.

Examples of the kit and process of this invention are given below. These examples are not to be taken as exclusive of the scope of the invention, but merely set forth specific preferred examples presently known which will serve to elucidate and render more easily understood the present invention:

EXAMPLE 1

A cotton pad is provided having major dimensions of 2 inches on each side and a thickness of approximately ¼ inch, and formed of long staple natural cotton fibers. The pad is initially washed in warm methyl alcohol with 1% pyridine to remove any oils or hemi-celluloses and then dried. The dried pad is then dipped into a solution of 100 milliliters of methyl alcohol containing in solution, the following catalysts and enhancing agents:

Catalyst: accelerator-diethanolamine HCl—0.3 gram; and
Imidazole—0.1/100 ml

The pad was fully saturated with the methanol solution, permitted to drip dry and then to air dry completely.

Five grams of methyl 2-cyanoacrylate containing 0.085% hydroquinone is uniformly added to the top surface of the pad. The pad is connected to a thermocouple device for continuously reading the temperature of the pad. Within the first minute, the temperature of the pad rises to approximately 100° C.; within three minutes thereafter a fingerprint on a vertical wall surface located approximately 1 foot directly above the pad has developed so as to show the fingerprint form, but being translucent and not fully clarified.

EXAMPLE 2

The procedure of Example 1 was followed except that the cotton pad was saturated with a mixture containing 0.3 gram diethanolamine HCl, 2 grams toluene sulphonyl chloride and 1½ gram p-toluene sulphonyl hydrazide (tosyl hydrazide) in 100 milliliters of methanol. In addition, there was added 0.01-0.5 gram of fluorescamine and 1 gram trimethyl silyl imidazole to the 100 milliliters of methanol with which the pad was saturated. The cyanoacrylate compound used was ethyl 2-cyanoacrylate and the developed fingerprints located four feet from the pad, had the following characteristics:

A very faint bluish color, opaque with very fine details of ridges; the prints were hard and durable, and not easily removed from the substrate.

EXAMPLE 3

The procedure of Example 2 was followed except that the methanol solution, per 100 milliliters, contained:

p-toluene sulphonyl hydrazide (tosyl hydrazide)—0.5 gram
nicotinic acid hydrazide—0.5 gram
isonicotinic acid hydrazide—2 grams
p-toluene sulphonyl chloride—2 grams The pad was dipped into 200 milliliters of the above anhydrous methanol solution.

The developed fingerprint had the following characteristics:

an opaque white appearance with fine detail; the prints were durable.

EXAMPLE 4

The procedure of Example 2 was followed, except that the cotton pad was saturated with the following mixture of 100 ml. of methanol:

trimethylsilyl acetamide—0.5 gram
trimethylsilyl imidazole—0.5 gram
diethanolamine HCl—0.5 gram
o-phthaldehyde—1.0 gram
DMSO—1.0 gram A bluish-white print was obtained, having fine detail, and which fluoresced under ultraviolet light.

EXAMPLE 5

The procedure of Example 2 was followed, except that the cotton pad was saturated with the following mixture dissolved in 100 ml. of methanol:

TMSI-S reagent—1.0 gram
tetramethyl piperidine—0.5 gram
imidazole HCl—0.5 gram
toluene sulfonyl chloride—1.0 gram
fluorescamine—0.1 gram
o-phthaldehyde—0.5 gram Further, only 4 grams of the methylcyanoacrylate was added to the pad.

Finely detailed prints, having an opaque white appearance were obtained.

EXAMPLE 6

The procedure of Example 2 was followed, except that the cotton pad was saturated with the following mixture in 100 ml. of methanol:

diethanolamine HCl—0.5 gram
isonicotinic hydrazide—3.0 gram
trimethylsilyl imidazole—1.0 gram A bluish-white print was obtained, having fine detail, and which was visible under ordinary light.

EXAMPLE 7

The procedure of Example 2 was followed, except that the cotton pad was saturated with the following mixture in 100 ml. of methanol:

diethanolamine HCl—0.5 gram
trimethylsilyl acetamide—2.0 gram

A bluish-white print was obtained, having fine detail, and which was visible under ordinary light.

EXAMPLE 8

The procedure of Example 4 is followed, except that the pad is formed of flax fibers. The same results are obtained.

What is claimed is:

1. Kit means for the development of latent fingerprints from a solid surface, in kit form, the kit comprising a container containing, in liquid form, a polymerizable cyanoacrylate monomer, or polymer precursor, and a polymerization inhibitor admixed with the polymerizable cyanoacrylate monomer or polymer precursor, and in a separate container an inert pad having sorbed therewith at least one catalyst for the polymerization of such cyanoacrylate monomer, or polymer precursor, and a fingerprint development enhancer, sorbed with the inert pad, the enhancer having a vapor pressure in the temperature range of from about 80° to 140° C. and having suitable chemical and physical compatibility so as to be carried together with any cyanoacrylate microcrystalline vapor generated by the pad when contacted with the polymerizable cyanoacrylate monomer or polymer precursor.

2. The kit of claim 1 wherein the inert pad is formed of an inert, natural cellulosic fibrous material.

3. The kit of claim 2 wherein the inert fibrous material is selected from the group consisting of cotton and flax.

4. The kit of claim 1, wherein the enhancer is a low melting organic hydrazide.

5. The kit of claim 1, wherein the enhancer is a silization agent.

6. The kit of claim 1 wherein the enhancer is selected from a group consisting of low melting organic hydrazides, fluorescent labeling compounds, and silization agents.

7. The kit of claim 6 wherein the silization agents are selected from the group consisting of trimethyl silanes and dimethyl silanes.

8. The kit of claim 6 comprising a hydrogen chloride salt compound sorbed with the inert pad.

9. In a process for developing latent fingerprints on a solid surface, the process comprising contacting on a sorbent solid surface, a polymerizable cyanoacrylate monomer or polymer precursor, previously admixed with a polymerization inhibitor, and a polymerization catalyst, the polymerization catalyst being sorbed with the sorbent solid surface prior to the contacting with the monomer, or polymer precursor; in an amount and in a concentration sufficient to maintain an exothermic polymerization reaction so as to increase the temperature of the reagents and of the solid surface to at least about 80° C. for a period of at least about 3 minutes so as to generate a cyanoacrylate microcrystalline vapor; permitting said vapor to be conveyed to a surface containing a latent fingerprint; and permitting the development of the latent fingerprint by the cyanoacrylate microcrystalline vapor; the improvement which comprises the presence with the sorbent solid surface, or polymer precursor, of a fingerprint development enhancer selected from the group consisting of fluorescent amino acid labeling compounds, silization agents, hydrazide compounds, and amino acid indicator compounds, each of the enhancing compounds having a sufficient vapor pressure at a temperature in the range of between about 80° and 140° C., in the presence of cyanoacrylate microcrystalline vapor, to be carried together with the microcrystalline vapor to the location of the latent fingerprints.

10. The process of claim 9, wherein the enhancer is a hydrazide compound.

11. The process of claim 9, wherein the enhancer is a silization agent.

12. The process of claim 9 wherein the temperature of the reagents and of the solid surface is increased to a temperature of not greater than about 100° C.

13. The kit of claim 6 wherein the enhancer is a low melting organic hydrazide having the formula:

$$R_1-N=N-R_2,$$

wherein each of $R_1$ and $R_2$ is a hydrogen atom, aryl group, or a halogen atom.

14. The kit of claim 1 wherein the enhancer is a silization agent, and wherein the silization agent is an alkyl silyl compound having the formula:

$$CH_3-\underset{\underset{CH_3}{|}}{\overset{\overset{R_1}{|}}{Si}}-R$$

wherein $R_1$ is hydrogen, a methyl group, or substituted methyl group and R is a halogen atom, a carbamide group, an azine, or an aromatic group.

* * * * *